US00PP16244P2

(12) United States Plant Patent
Zonneveld

(10) Patent No.: US PP16,244 P2
(45) Date of Patent: Feb. 7, 2006

(54) ***AGAPANTHUS* PLANT NAMED 'BACK IN BLACK'**

(50) Latin Name: *Agapanthus africanus*
Varietal Denomination: Back in Black

(75) Inventor: Piet Johannes Hendrikus Zonneveld, Voorhout (NL)

(73) Assignee: Witteman & Co., Hillegom (NL)

( * ) Notice: Subject to any disclaimer, the term of this patent is extended or adjusted under 35 U.S.C. 154(b) by 15 days.

(21) Appl. No.: 10/968,805

(22) Filed: Oct. 19, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Agapanthus* plant named 'Back in Black' characterized by its strong, mostly upright, long and black-colored scapes; umbels with numerous violet blue-colored flowers; and freely flowering habit.

2 Drawing Sheets

Botanical classification/cultivar designation: *Agapanthus africanus* cultivar Back in Black.

BACKGROUND OF THE INVENTION

The present Invention relates to a new and distinct cultivar of *Agapanthus* plant, botanically known as *Agapanthus africanus,* and hereinafter referred to by the name 'Back in Black'.

The new *Agapanthus* originated from a chance open-pollination of a group of unnamed selections of *Agapanthus africanus,* not patented, in 1998. The cultivar Back in Black was discovered and selected by the Inventor as a flowering plant within the resultant progeny of the chance open-pollination in a controlled environment in Lisse, The Netherlands in 2000.

Asexual reproduction of the new *Agapanthus* by cuttings in a controlled environment in Lisse, The Netherlands since 2000, has shown that the unique features of this new *Agapanthus* are stable and reproduced true to type in successive generations.

SUMMARY OF THE INVENTION

The cultivar 'Back in Black' has not been observed under all possible environmental conditions. The phenotype may vary somewhat with variations in environment such as temperature and light intensity without, however, any variance in genotype.

The following traits have been repeatedly observed and are determined to be the unique characteristics of 'Back in Black'. These characteristics in combination distinguish 'Back in Black' as a new and distinct cultivar of *Agapanthus:*

1. Strong, mostly upright, long and black-colored scapes.
2. Umbels with numerous violet blue-colored flowers.
3. Freely flowering habit.

Compared to plants of the female parent selection, plants of the new *Agapanthus* are more compact, are more freely flowering and differ in flower coloration.

Plants of the new *Agapanthus* can be compared to plants of the cultivar Intermedia, not patented. In side-by-side comparisons conducted in Lisse, The Netherlands, plants of the new *Agapanthus* differed from plants of the cultivar Intermedia, in the following characteristics:

1. Plants of the new *Agapanthus* were more compact than plants of the cultivar Intermedia.
2. Scapes of plants of the new *Agapanthus* were all black in color whereas scapes of plants of the cultivar Intermedia were only black in random areas.
3. Plants of the new *Agapanthus* were more freely flowering than plants of the cultivar Intermedia.
4. Plants of the new *Agapanthus* and the cultivar Intermedia differed in flower color.

DESCRIPTION OF THE PHOTOGRAPHS

The accompanying colored photographs illustrate the overall appearance of the new *Agapanthus,* showing the colors as true as it is reasonably possible to obtain in colored reproductions of this type. Colors in the photographs may differ slightly from the color values cited in the detailed botanical description which accurately describe the colors of the new *Agapanthus.*

The photograph at the top left on the first sheet comprises a side perspective view of a typical flowering plant of 'Back in Black'.

The photograph at the top right of the first sheet is a close-up view of a typical scape and pedicels of 'Back in Black'.

The photograph at the bottom of the first sheet is a close-up view of typical leaves of 'Back in Black'.

The photograph at the top of the second sheet is a close-up view of a typical flowering inflorescence of 'Back in Black'.

The photograph at the bottom of the second sheet is a close-up view of a typical flower of 'Back in Black'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe one-year old plants grown in Lisse, The Netherlands under commercial practice in an outdoor nursery. During the production of the plants, day temperatures ranged from 14 to 33° C. and night temperatures ranged from 8 to 14° C. Measurements and numerical values represent averages for typical flowering plants. The photographs and the description were taken during the late summer.

Botanical classification: *Agapanthus africanus* cultivar Back in Black.

Parentage: Chance open-pollination of a group of unnamed selections of *Agapanthus africanus,* not patented.

Propagation:

*Type.*—By cuttings.

*Time to initiate roots.*—About 30 days at 20° C.

*Root description.*—Thick, fleshy; whitish gray in color. Bulb production has not been observed.

*Rooting habit.*—Freely branching; dense.

Plant description:

*Plant form/growth habit.*—Upright flowering plant. Leaves basal with central flowering scape with flowers arranged in umbels. Moderately vigorous growth habit.

*Crop time.*—Usually about four months are required to produce finished flowering plants in containers.

*Plant height, soil level to top of foliar plane.*—About 15 cm.

*Plant height, soil level to top of inflorescence.*—About 50 cm.

*Plant width.*—About 34 cm.

*Leaves.*—Arrangement: Simple; basal; 2-ranked; sessile. Quantity of leaves per plant: About 18. Length: About 15.6 cm. Width: About 1.8 cm. Shape: Linear. Apex: Acute. Base: Cuneate. Margin: Entire. Texture, upper and lower surfaces: Glabrous, smooth; relatively thick and leathery. Venation pattern: Parallel. Color: Developing and fully expanded leaves, upper surface: 137A. Developing and fully expanded leaves, lower surface: 137B; towards the base, N187A. Venation, upper and lower surfaces: 137A.

Flower description:

*Flowering habit.*—Inflorescences scapose with single campanulate flowers; flowers arranged in umbels on long, mostly erect and strong scapes. Flowers not fragrant; flowers persistent. Flowers face outwardly to slightly upright.

*Natural flowering season.*—Plants flower during the summer in The Netherlands.

*Flower longevity on the plant.*—About one week.

*Inflorescence size.*—Length: About 6 cm. Width: About 14.7 cm.

*Flower buds.*—Length: About 2.5 cm. Diameter: About 7 mm. Shape: Ovoid. Color: N92B.

*Flowers.*—Quantity of flowers per inflorescence: About 35; typically two flowering stems develop per plant. Shape: Campanulate. Diameter: About 2.8 cm. Depth (height): About 3 cm.

*Perianth.*—Quantity/arrangement: Eight tepals per flower; fused at base. Tepal length: About 3 cm; lower 1.2 cm of the tepals is fused. Tepal width: About 7 mm. Tepal shape: Oblanceolate. Tepal apex: Broadly acute. Tepal margin: Entire. Tepal texture, upper and lower surfaces: Smooth, glabrous. Tepal color: When opening, upper surface: 93A. When opening, lower surface: N89B; towards the center, N92B. Fully opened, upper surface: 93A; stripes, 94A to 94C; color becoming closer to 86A with development. Fully opened, lower surface: N89B; towards the center, N92B.

*Scape.*—Angle: Mostly erect to about 40° from vertical. Strength: Strong. Length: About 44 cm. Diameter: About 5 mm. Texture: Smooth, glabrous. Color: Very close to 202A, covered with a waxy layer, 202B.

*Pedicels.*—Angle: Erect to horizontal to the scape. Strength: Strong. Length: About 5 cm. Diameter: About 1.5 mm. Texture: Smooth, glabrous. Color: Very close to 202A, covered with a waxy layer, 202B.

*Reproductive organs.*—Stamens: Quantity per flower: Six. Filament length: About 1.8 cm. Filament color: Close to 92A. Anther shape: Reniform. Anther length: About 1 mm. Anther color: 202A. Amount of pollen: Scarce. Pollen color: 202A. Pistils: Quantity per flower: One. Length: About 2 cm. Stigma shape: Narrowly clavate. Stigma color: 90A. Style length: About 2 cm. Style color: Close to 90A. Ovary color: 145B.

*Fruits.*—Quantity per flower: One. Length: About 1.6 cm. Diameter: About 6 mm. Texture: Smooth. Color: 143B.

*Seeds.*—Length: About 1.5 mm. Diameter: About 1 mm. Color: 202A.

Disease/pest resistance: Resistance to pathogens and pests common to *Agapanthus* has not been determined.

Temperature tolerance: Plants of the new *Agapanthus* have been observed to tolerate high temperatures of 40° C. and have been observed to be hardy to USDA Zone 8.

It is claimed:

1. A new and distinct cultivar of *Agapanthus* plant named 'Back in Black', as illustrated and described.

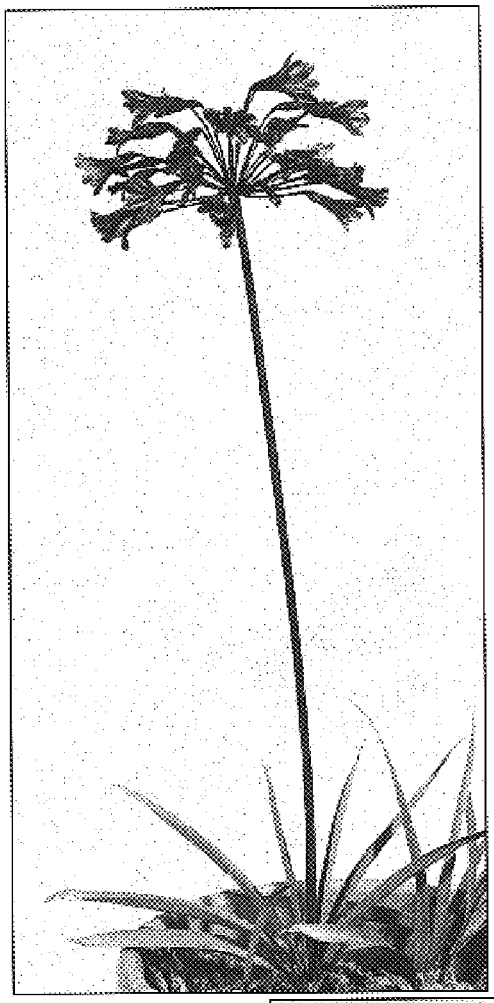
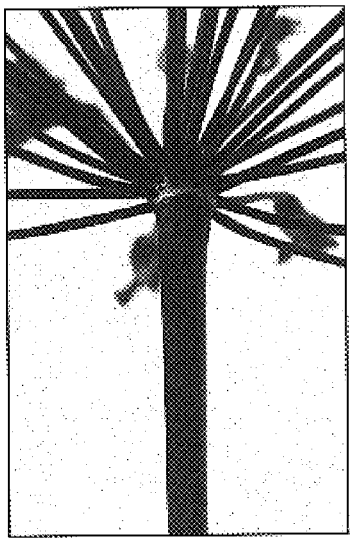
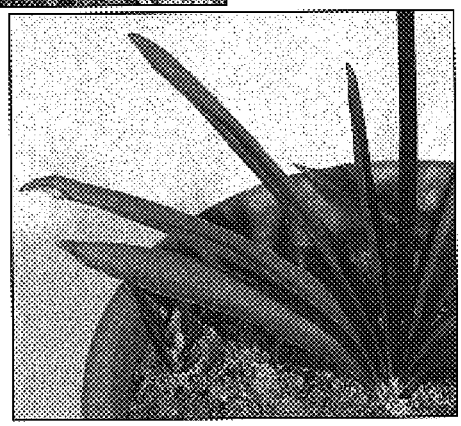

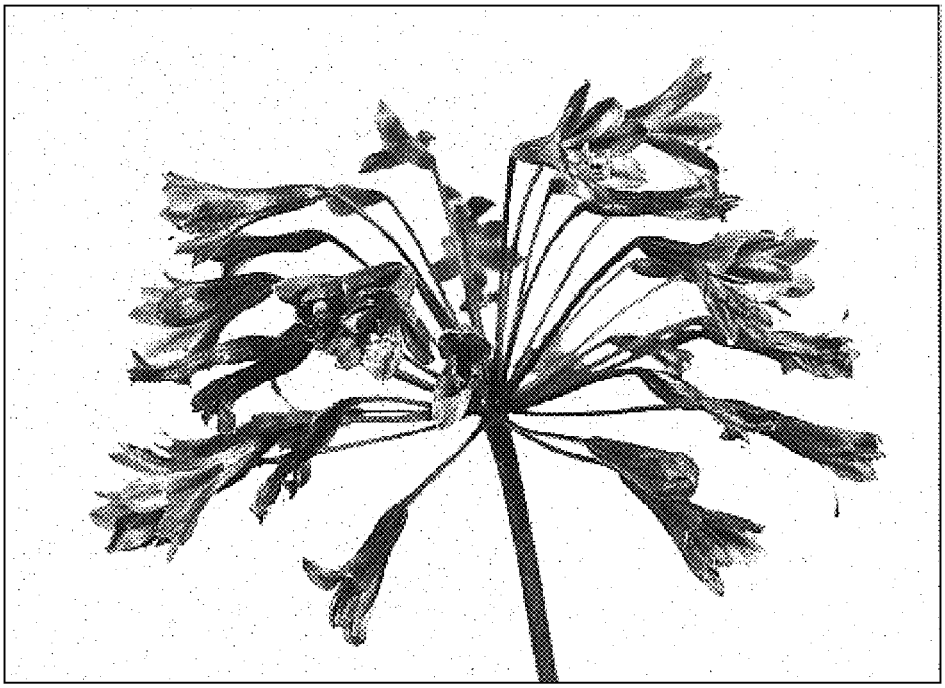
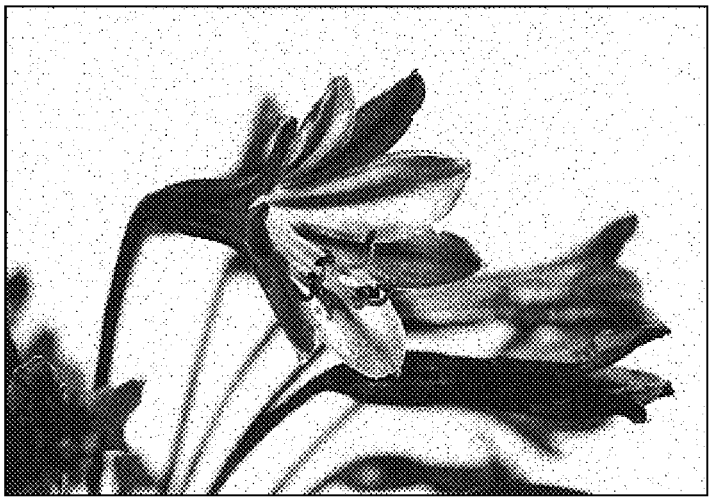

* * * * *